(12) United States Patent
Hermle et al.

(10) Patent No.: US 9,314,563 B2
(45) Date of Patent: Apr. 19, 2016

(54) HANDLE FOR A MEDICAL INSTRUMENT

(71) Applicant: Karl Storz GmbH & Co. KG, Tuttlingen (DE)

(72) Inventors: Rainer Hermle, Gosheim (DE); Robin Merz, Furtwangen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 533 days.

(21) Appl. No.: 13/717,263

(22) Filed: Dec. 17, 2012

(65) Prior Publication Data

US 2013/0158467 A1 Jun. 20, 2013

(30) Foreign Application Priority Data

Dec. 17, 2011 (DE) .......................... 10 2011 121 498

(51) Int. Cl.
*A61M 1/00* (2006.01)
*A61M 3/02* (2006.01)
*A61B 1/00* (2006.01)
*A61B 17/00* (2006.01)

(52) U.S. Cl.
CPC .......... *A61M 3/0283* (2013.01); *A61B 1/00128* (2013.01); *A61B 17/00234* (2013.01); *A61B 2017/00477* (2013.01); *A61B 2217/005* (2013.01); *A61B 2217/007* (2013.01)

(58) Field of Classification Search
CPC ............... A61M 3/002; A61M 3/0283; A61B 2217/0055; A61B 2217/007; A61B 1/00128; A61B 2017/00477; A61B 17/00234

USPC .................................... 604/27; 433/126, 131
See application file for complete search history.

(56) References Cited

U.S. PATENT DOCUMENTS 4,279,596 A * 7/1981 Weber ........................... 433/126
5,052,725 A 10/1991 Meyer et al.

FOREIGN PATENT DOCUMENTS

| AT | 41820 T | 4/1989 |
|---|---|---|
| DE | 19805532 A1 | 8/1998 |
| DE | 102004050852 A1 | 5/2006 |
| DE | 102006016211 A1 | 10/2007 |
| EP | 0151519 A1 | 8/1985 |
| EP | 2382940 A2 | 11/2011 |

* cited by examiner

*Primary Examiner* — Theodore Stigell
*Assistant Examiner* — Tiffany Legette
(74) *Attorney, Agent, or Firm* — Whitmyer IP Group LLC

(57) ABSTRACT

A handle for a medical instrument having a handle housing and a connection adapter for hose and/or tube connections, which can be inserted into the handle housing. The connection adapter can be inserted fluid-tight into a corresponding support recess of the handle housing by at least one connection support and such that a surrounding ring groove for inserting a sealing element is positioned on the at least one connection support. It is proposed that at least two surrounding ring grooves, mounted one behind the other, should be configured on the connection support in the axial direction of the at least one connection support, such that the connection support has a constant outer diameter in the area of the at least two ring grooves and such that a sealing element, is positioned at least in the first ring groove, looking from the free end of the connection support.

9 Claims, 3 Drawing Sheets

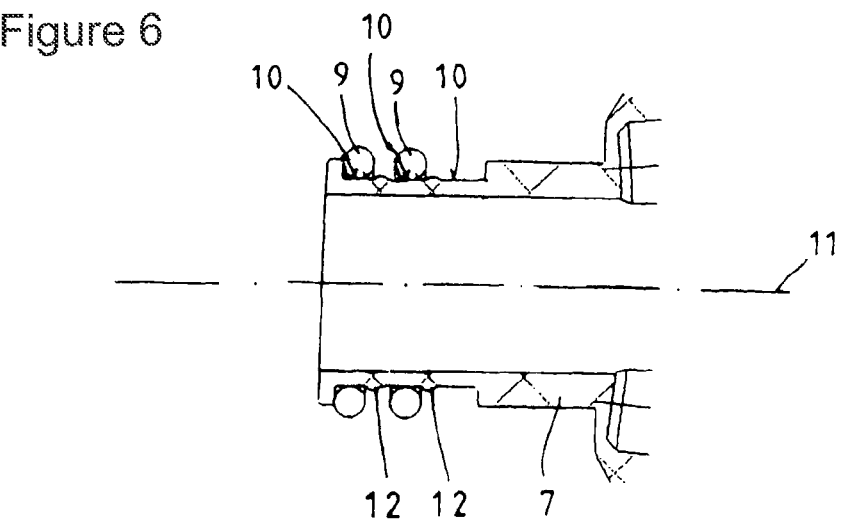
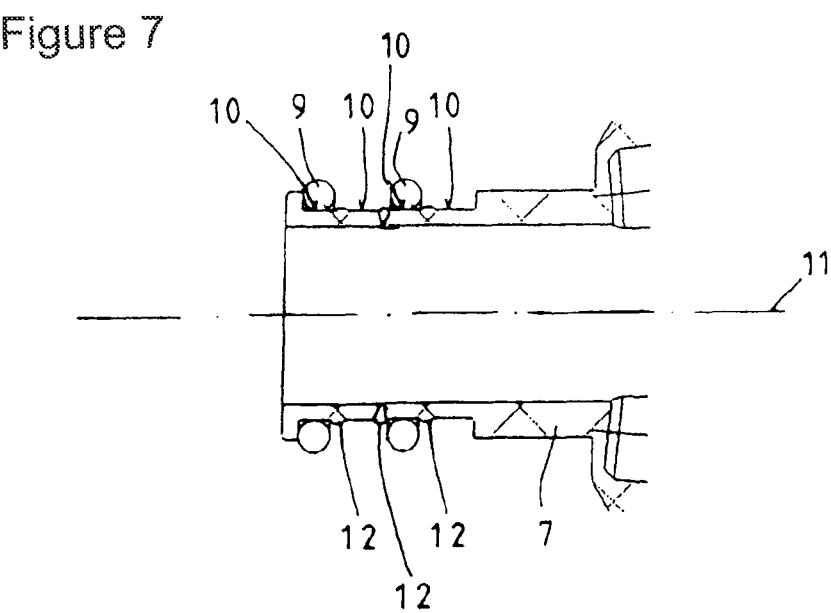

HANDLE FOR A MEDICAL INSTRUMENT

FIELD OF THE INVENTION

The invention relates to a handle for a medical instrument having a handle housing and a connection adapter for hose and/or tube connections, which can be inserted into the handle housing, such that the connection adapter can be inserted fluid-tight by at least one connection support into a corresponding support recess in the gripping housing and such that a surrounding ring groove is mounted on the at least one connection support to receive a sealing element.

BACKGROUND OF THE INVENTION

Suction and irrigation handles for medical instruments are known in the art in various embodiments. Irrigating fluid issuing from an external irrigation fluid source and fed to the distal end of the medical instrument by the handle serves during the surgical procedure, among other uses, to irrigate the surgical site as well as to cleanse an endoscope lens in order to ensure that the operator has a constantly undisturbed view of the surgical area. Irrigating fluid and also blood are suctioned out of the surgical area via a suction channel, such that the suction channel is connected by the handle to an external suction apparatus.

Hose lines serving to connect the handle with the external irrigating fluid source and external suction apparatus are secured proximally on the handle side to a connection adapter mounted in the handle housing. The connection adapter is inserted fluid-tight into a support recess of the handle housing by a connection support mounted on the distal end of the connection adapter.

Because the connection adapter can be cleansed only poorly or not at all completely, the connection adapter as a rule is configured as a replaceable disposable part in order to be able to insert and withdraw it again easily. In handles known in the art, fluid-tight seal in the area of the connection support of the connection adapter is provided by a sealing element that is preferably configured as an O-ring and is mounted in a ring groove of the connection support.

The problem in using the O-ring seal is that, upon insertion of the connection support into the support recess of the handle housing, the O-ring generates gliding friction, which makes insertion difficult or even impossible because of the very small structural size of the medical instrument.

SUMMARY OF THE INVENTION

Consequently it is the object of the invention to provide a handle of the aforementioned type, whose connection adapter ensures not just ease of installation and dismantling but also a fluid-tight connection.

This object is achieved according to the invention in that at least two surrounding ring grooves are configured on the connection support, positioned one behind the other, in the axial direction of the at least one connection support, such that the connection support has a constant outer diameter in the area of the at least two ring grooves, and that a sealing element, in particular an O-ring, is positioned at least in the first ring groove as viewed from the free end of the connection support.

Because of the inventive arrangement of the at least two surrounding ring grooves arranged behind one another and of the at least one sealing element mounted in the most distally located ring groove, upon inserting the connection support into the support recess, the resulting gliding friction between the surface of the sealing element and the inside of the support recess is used to push or roll the sealing element from the first ring groove into the second. In this manner the resistance on inserting the connection adapter into the handle housing is reduced and the sealing element is nevertheless held in a precisely defined fluid-tight sealing position.

Because, on the one hand, the connection adapters produced as disposable parts are as a rule injection-molded parts that have higher tolerances in terms of production than milled or turned parts and, on the other hand, the sealing elements configured as O-rings are likewise not configured as single units, the interaction of groove and O-ring is especially ill defined. Only through the inventive configuration of the second ring groove into which the sealing element is moved during installation, is it possible to ensure the required fluid-tightness of the handle.

To cause the sealing element configured preferably as O-ring not merely to be axially pushed into the second ring groove in the transition from the first ring groove, but instead to roll from the one ring groove into the other ring groove, it is proposed according to a preferred configuration of the invention that the ring grooves arranged behind one another should be separated from one another by a blocking element in each case, said blocking element advantageously being configured as a radial mound. Because the blocking element is configured as only very small in relation to the sealing element, that is, narrow in the axial direction and radially flat, the force required to push or roll the sealing element over the blocking element is relatively small. By the motion of inserting the connection support into the support recess, the sealing element is pressed against the blocking element and rotates by at least half its circumference. To return to normal condition, the sealing element "jumps," so to speak, into the second ring groove, so that the sealing element, with the connection adapter fully inserted, after about one full rotation is seated firmly and well-sealing in the second ring groove.

The ring grooves positioned behind one another are advantageously positioned parallel to one another; however, it is also possible to arrange the ring grooves to run diagonal to one another.

With a practical embodiment of the invention it is proposed that the ring grooves should be configured equal in width and equally deep to one another in the radial direction in order to ensure a defined position of the sealing element in the respective ring groove.

According to a practical embodiment of the invention, it is proposed that two surrounding ring grooves positioned parallel to one another in the axial direction should be configured on the connection support and that a sealing element configured as an O-ring should be positioned in the ring groove that is in front on the distal end.

It is finally proposed with the invention that the connection adapter should be capable of being replaceably secured in the handle housing. The replaceable configuration of the connection adapter makes it possible to configure the connection adapter as a disposable part, which can be dismantled and discarded after each treatment, because sterile cleaning of it would scarcely be possible or else only at considerable cost.

To ensure fluid-tight seal of the connection adapter, it is proposed with the invention that, upon inserting the connection support of the connection adapter into the support recess of the handle housing, the at least one sealing element should be capable of being conveyed from its position in the respective ring groove into a ring groove that is directly adjoining toward the proximal end in the axial direction of the connection support.

It is further proposed with the invention that the at least one sealing element should be capable of being transferred back into the original ring groove upon withdrawing the connection support of the connection adapter from the support recess of the handle housing. Because of the reversible return of the at least one sealing element into its original ring groove, it is ensured that the fluid-tightness is guaranteed again even upon renewed insertion of the connection adapter.

Other features and advantages of the invention can be seen from the appended drawings in which three embodiments of an inventive handle are depicted only in exemplary manner, without restricting the invention to these embodiments.

BRIEF DESCRIPTION OF THE DRAWINGS

FIG. 6 shows a depiction according to FIG. 3, but showing a second inventive embodiment.
FIG. 7 shows a depiction according to FIG. 3, but showing a third inventive embodiment.

DETAILED DESCRIPTION OF THE INVENTION

Figure 1:
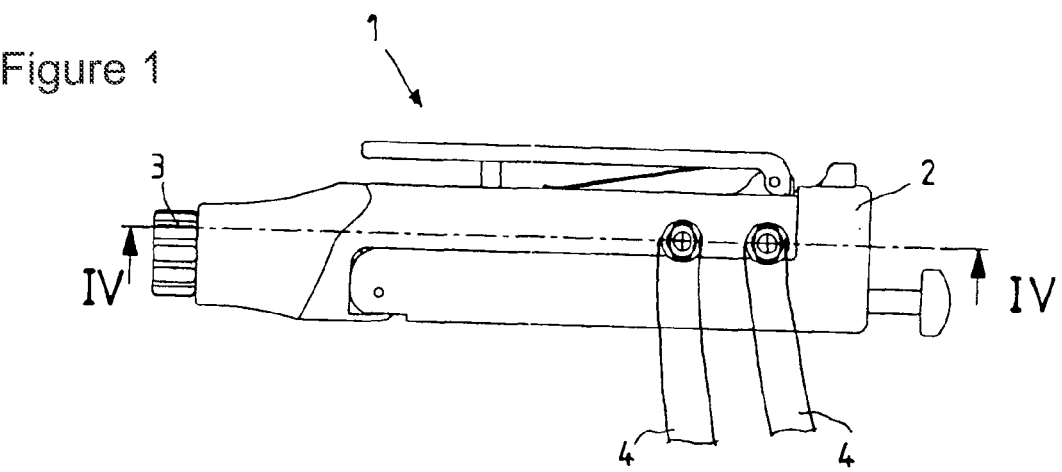
FIG. 1 shows a side view of an inventive handle.

FIG. 1 shows a handle 1 for a medical instrument that is not further depicted. The handle 1 comprises a handle housing 2 on whose distal end, for example, a screw-on coupling 3 is mounted in order to connect the handle 1 with the shaft of a medical instrument.

The illustrated handle 1 is a suction-irrigation handle 1 as is used, for example, in endoscopic surgery. Suction-irrigation handles 1 serve to conduct irrigation fluid via a hollow shaft to the surgical area of the medical instrument and to suction fluid out of the surgical area. Irrigation fluid issuing from an external irrigation fluid source and conveyed to the distal end of the medical instrument serves, among other purposes, to cleanse an endoscope lens in order to ensure the operator a constantly undisturbed view of the surgical area. Irrigating fluid and also blood are suctioned out of the surgical area via an irrigation channel, such that the irrigation channel of the medical instrument is connected to an external irrigation apparatus, not illustrated, by the handle 1.

To connect the handle 1 with the external irrigation fluid source and the external irrigation apparatus, use is made of hose lines 4, which are secured proximally on the handle side to a connection adapter 5 positioned in the handle housing 2, for which purpose hose connections 6 are configured on the connection adapter 5. The connection adapter 5 is inserted fluid-tight into a support recess 8 of the handle housing 2 by a connection support 7 positioned distally on the connection adapter 5.

Because the connection adapter 5 can be cleansed only poorly or not at all completely, the connection adapter 5 is configured as a replaceable disposable part.

The fluid-tight seal in the area of the connection support 7 of the connection adapter 5 and of the support recess 8 of the handle housing 2 is achieved by a sealing element 9 that is preferably configured as an O-ring and that is positioned in a ring groove 10 of the connection support 7.

Figure 2:
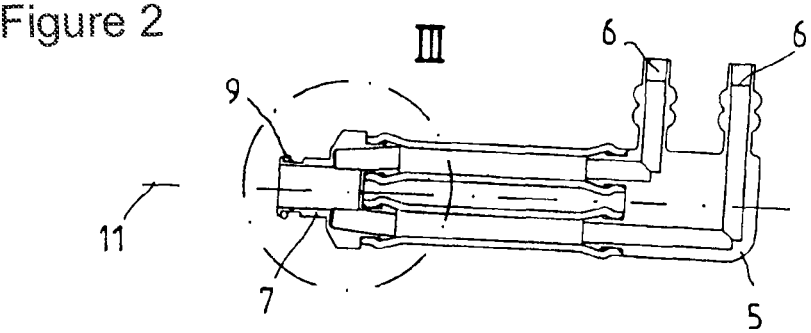
FIG. 2 shows an overhead view of a connection adapter according to a first inventive embodiment.
Figure 3:
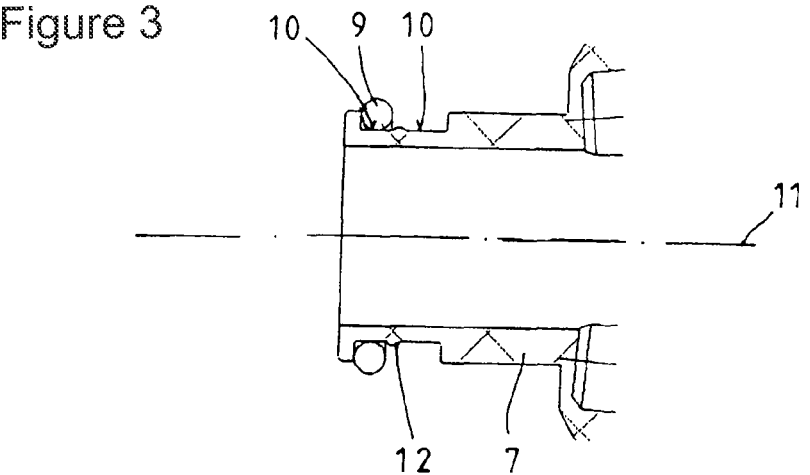
FIG. 3 shows an enlarged view of detail III from FIG. 2.

The structural configuration of the connection adapter 5, as well as of the connection support 7 equipped with the sealing element 9, can be seen in particular from FIGS. 2 and 3.

The connection adapter 5 depicted in FIG. 2 is a Y-shaped connection adapter 5 that comprises two hose connections 6 for hose lines 4 on the proximal side and one connection support 7 on the distal side for contacting with the support recess 9 of the handle housing 2. It is also possible to construct alternative configurations with more or fewer hose connections 6 as well as several connection supports 7. It is likewise possible to dispose the connection support or supports 7 and/or the hose connection or connections 6 in a different spatial arrangement on the connection adapter 5.

The structure of the sealing arrangement on the connection support 7 can be seen from FIG. 3. In the illustrated embodiment, two surrounding ring grooves 10 arranged parallel to one another are configured on the connection support 7 in the axial direction of the connection support 7, such that the two ring grooves 10 are configured as equally deep in the radial direction. With the connection adapter 5 in the position shown in FIGS. 2 and 3 and not yet inserted into the handle housing 2, the sealing element 9 configured as an O-ring is positioned in the first ring groove 10 looking from the free end of the connection support 7.

Alternatively to arranging the two ring grooves 10 parallel to one another, it is also possible to dispose the ring grooves diagonally to one another.

The two ring grooves 10 disposed parallel to one another are separated by a blocking element 12 configured as a radial mount.

Because of the arrangement of the two surrounding ring grooves 10 disposed parallel to one another and the sealing element 9 positioned in the frontmost ring groove 10 on the distal end, upon inserting the connection support 7 into the support recess 8 the resulting gliding friction between the surface of the sealing element 9 and the inside of the support recess 8 is used to push the sealing element 9 from the first ring groove 10 into the second ring groove 10. In this way the resistance upon inserting the connection adapter 5 into the handle housing 2 is reduced and the sealing element 9 is nevertheless retained in a precisely defined fluid-tight sealing position.

Figure 4:
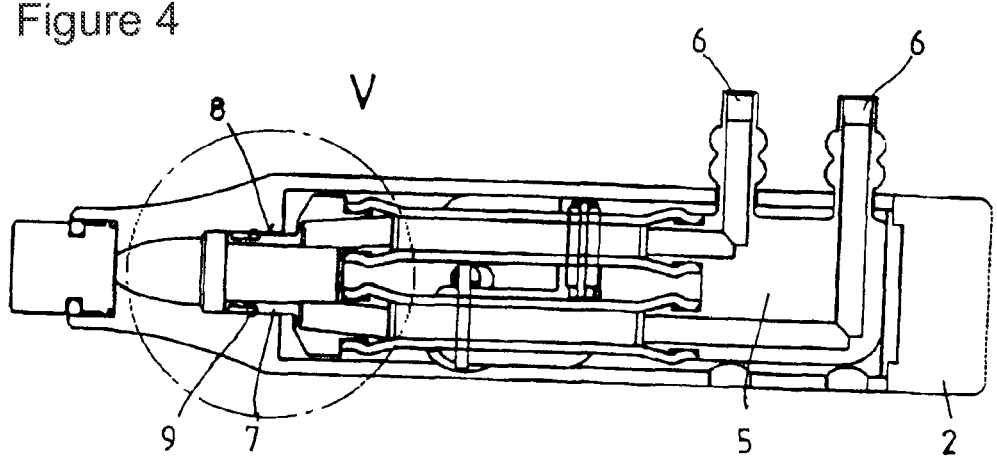
FIG. 4 shows a section along the line IV-IV from FIG. 1.
Figure 5:
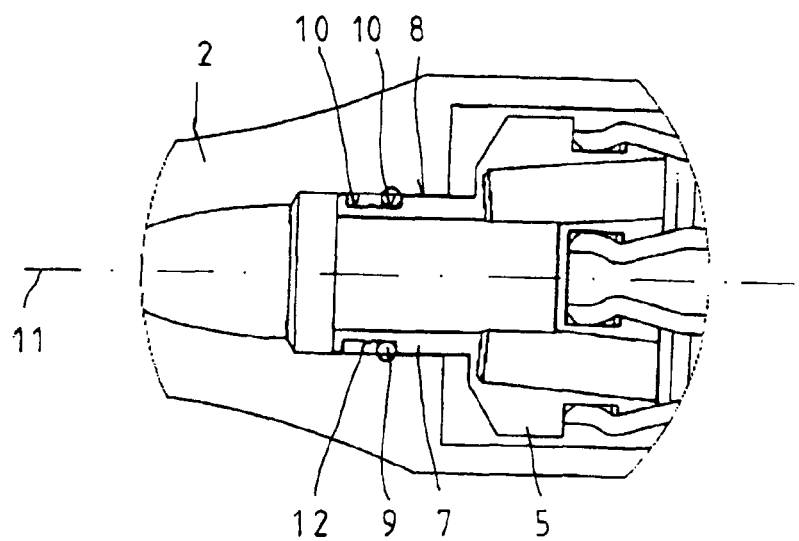
FIG. 5 shows an enlarged view of detail V from FIG. 4.

Because the blocking element 12 is configured as only very small in relation to the sealing element 9, that is, narrow in the axial direction and radially flat, the force required to push the sealing element 9 over the blocking element 12 is relatively small. By the movement of inserting the connection support 7 into the support recess 8, the sealing element 9 is pressed against the blocking element 12 and rotates by about half of its circumference. To return to the normal position again, the sealing element 9 "jumps," so to speak, into the second ring groove 10 so that, with the connection adapter 5 completely inserted into the handle housing 2, the sealing element 9 after a complete rotation is seated, sealing firmly and correctly, in the second ring groove 10, as can be seen from FIGS. 4 and 5.

As can be seen further from FIGS. 2 through 5, the connection support 7 in the area of the two ring grooves 10 has a constant outer diameter in order to ensure a constant force for transferring the sealing element 9 from the first ring groove 10 into the other ring groove 10.

To ensure a define position of the sealing element 9 in the respective ring groove 10, both ring grooves 10 are configured as equally wide and, in radial direction, equally deep.

In disassembling the connection adapter 5 from the handle housing 2, the sealing element 9 upon withdrawing the connection support 7 from the support recess 8 is pressed against the blocking element by the movement of withdrawing the connection support 7 from the support recess 8, and rotates by half of its circumference. To return to normal position, the sealing element "jumps," so to speak, back into the first ring groove 10 so that the force upon inserting the connection adapter 5 is exactly as great as upon withdrawing the connection adapter 5.

Alternatively to the illustrated embodiment of the connection support 7 with two surrounding ring grooves 10 and one sealing element 9, configurations with more ring grooves 10 and more sealing elements 9 are also possible.

Below, with reference to FIGS. 6 and 7, two alternative embodiments for configuring the connection supports 7 are described by way of example:

Alternative 1 according to FIG. 6:

A connection support 7 with three parallel ring grooves 10 and two sealing elements 9 that are disposed in such a way that the sealing elements 9 are transferred from the first and second ring grooves 10 into the second and third ring grooves 10 upon assembling the connection adapter 5.

Alternative 2 according to FIG. 7:

A connection support 7 with four parallel ring grooves 10 and two sealing elements 9 that are disposed in such a way that the sealing elements 9 are transferred from the first and third ring grooves 10 into the second and fourth ring grooves 10 upon assembling the connection adapter 5.

The configuration of the connection support 7 as described above has the advantage that the rolling friction, which occurs upon inserting the connection support 7 of the connection adapter 5 into the support recess 8 of the handle housing 2 and transfers the sealing element 9 from the front ring groove 10 to the rear ring groove 10, facilitates insertion of the connection adapter 5 into the handle housing 2.

Because of this rolling friction of the sealing element 9, it becomes possible to prevent the occurrence of the strong gliding friction that is known in the art and can lead to abrasion of the O-ring and thus to a poorly insulated instrument. In addition, the tolerated play between the sealing element 9, connection support 7 and support recess 8 is compensated by the rolling movement of the sealing element 9.

What is claimed is:

1. A handle for a medical instrument with a grip housing and a connecting adapter, which is insertable into the grip housing, for hose and/or pipe connections, wherein the connecting adapter is insertable in a fluid-tight manner into a corresponding nozzle receptacle of the grip housing via at least one connection nozzle, and on the at least one connection nozzle, a circumferential annular groove is arranged for receiving a sealing element, wherein, in the axial direction of the at least one connection nozzle, on the connection nozzle at least two circumferential annular grooves are formed, arranged one after the other, wherein the connection nozzle in the area of the at least two annular grooves has a constant outer diameter, and wherein, at least in the first annular groove, viewed from a free end of the connection nozzle that is insertable into the respective nozzle receptacle, the sealing element is arranged, characterized in that the second annular groove, in the axial direction of the connection nozzle, abuts proximally directly against the first annular groove and in that the at least one sealing element, at the time of the insertion of the connection nozzle of the connecting adapter into the nozzle receptacle of the grip housing is transferred, by sliding friction between the surface of the sealing element and the inside of the grip housing, from its position in the first annular groove into the second annular groove, and wherein the annular grooves, which are arranged one after the other, are separated from one another in each case by a stop element which is formed as a radial elevation which is narrow in the axial direction.

2. The handle according to claim 1, characterized in that the annular grooves, which are arranged one after another, are arranged parallel to one another.

3. The handle according to claim 1, characterized in that the annular grooves are formed so that they have the same width.

4. The handle according to claim 1, characterized in that the annular grooves are formed so that they have the same depth in the radial direction.

5. The handle according to claim 1, characterized in that, on the connection nozzle, the only two circumferential annular grooves formed are the first and second annular grooves, which are arranged parallel to each other in the axial direction.

6. The handle according to claim 1, characterized in that the connecting adapter is immobilized in a removable manner in the grip housing.

7. The handle according to claim 1, characterized in that, at the time when the connection nozzle of the connecting adapter is pulled out of the nozzle receptacle of the grip housing, the at least one sealing element is transferred back into the original annular groove.

8. The handle according to claim 1, characterized in that the sealing element comprises an O-ring.

9. The handle according to claim 1, characterized in that the radial elevation is radially flat.

* * * * *